United States Patent
Fitzpatrick et al.

(10) Patent No.: US 6,919,379 B2
(45) Date of Patent: Jul. 19, 2005

(54) COMPOUNDS USEFUL IN REFLUX DISEASE

(75) Inventors: Kevin Fitzpatrick, Albany, NY (US);
William Geiss, Albany, NY (US);
Anders Lehmann, Mölndal (SE);
Gunnel Sundén, Mölndal (SE);
Sverker Von Unge, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/479,763

(22) PCT Filed: Jun. 4, 2002

(86) PCT No.: PCT/SE02/01085

§ 371 (c)(1),
(2), (4) Date: Jan. 13, 2004

(87) PCT Pub. No.: WO02/100823

PCT Pub. Date: Dec. 19, 2002

(65) Prior Publication Data
US 2004/0152775 A1 Aug. 5, 2004

(30) Foreign Application Priority Data

Jun. 8, 2001 (SE) ................................................ 0102056
Dec. 20, 2001 (SE) ................................................ 0104342

(51) Int. Cl.⁷ ........................ A61K 31/13; C07C 313/00
(52) U.S. Cl. ....................................... 514/665; 562/126
(58) Field of Search ........................... 514/665; 562/126

(56) References Cited

U.S. PATENT DOCUMENTS

| 4,599,346 | A | * | 7/1986 | Schickaneder et al. ..... 514/317 |
| 5,036,057 | A | | 7/1991 | Martin |
| 5,162,364 | A | | 11/1992 | Debaert et al. |
| 5,214,063 | A | | 5/1993 | Debaert et al. |
| 5,278,166 | A | | 1/1994 | Debaert et al. |
| 6,576,626 | B2 | * | 6/2003 | Elebring et al. ............ 514/114 |

FOREIGN PATENT DOCUMENTS

| CH | 449046 | 12/1967 |
| EP | 0181833 A1 | 5/1986 |
| EP | 0356128 A2 | 2/1990 |
| EP | 0399949 A1 | 11/1990 |
| FR | 2722192 A1 | 1/1996 |
| WO | WO-87/04077 | 7/1987 |
| WO | WO-96/11680 | 4/1996 |
| WO | WO-98/11885 | 3/1998 |

OTHER PUBLICATIONS

Wolfgang Froestl et al., "Phosphinic Acid Analogues of GABA. 1. New Potent and Selective $GABA_B$ Agonists"; J. Med. Chem., 1995, 38, 3297–3312.

Nicholas I. Carruthers et al., "Synthesis of a Series of Sulfinic Acid Analogs of GABA and Evaluation of Their $GABA_B$ Receptor Affinities"; Bioorg. & Med. Chem. Lett. (1998), 8, 3059–3064.

Richard H. Holloway and John Dent, "Pathophysiology of Gastroesophageal Reflux"; Gastroenterology Clinics of North America, vol. 19, No. 3, Sep. 1990, p. 517–535.

* cited by examiner

Primary Examiner—Paul A. Zucker
(74) Attorney, Agent, or Firm—White & Case LLP

(57) ABSTRACT

Novel compounds of formula (I) wherein $R_1$ represents hydrogen; $R_2$ represents hydroxy, fluoro, or an oxo group; $R_3$ represents hydrogen; $R_4$ represents hydrogen; and pharmaceutically acceptable salts, solvates, and the stereoisomers thereof, with the exception of the racemate of (3-amino-2-hydroxypropyl)sulphinic acid. The compounds are useful in therapy, especially for the treatment of reflux disease. The invention is also related to processes for their preparation, intermediates of said process and pharmaceutical compositions containing said therapeutically active compounds and to the use of said active compounds in therapy

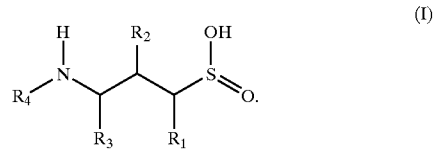

(I)

13 Claims, No Drawings

COMPOUNDS USEFUL IN REFLUX DISEASE

FIELD OF THE INVENTION

The present invention is related to novel compounds useful in therapy, especially for the inhibition of transient lower oesophageal sphincter relaxations and for the treatment of gastro-oesophageal reflux disease (GORD), as well as to their pharmaceutically acceptable salts, solvates and stereoisomers. The invention is also related to processes for their preparation, pharmaceutical compositions containing said therapeutically active compounds and to the use of said active compounds in therapy.

BACKGROUND OF THE INVENTION

Reflux

Gastro-oesophageal reflux disease (GORD) is the most prevalent upper gastrointestinal tract disease. Current therapy has aimed at reducing gastric acid secretion, or at reducing oesophageal acid exposure by enhancing oesophageal clearance, lower oesophageal sphincter tone and gastric emptying. The major mechanism behind reflux has earlier been considered to depend on a hypotonic lower oesophageal sphincter. However recent research (e.g. *Holloway & Dent* (1990). *Gastroenterol. Clin. N. Amer.* 19, 517–535) has shown that most reflux episodes occur during transient lower oesophageal sphincter relaxations, hereinafter referred to as TLOSR, i.e. relaxations not triggered by swallows. It has also been shown that gastric acid secretion usually is normal in patients with GORD.

Consequently, there is a need for compounds which reduce the incidence of TLOSR and thereby prevent reflux.

Pharmaceutical compositions comprising a local anaesthetic, adapted to inhibit relaxation of the lower oesophageal sphicter are disclosed in WO 87/04077 and in U.S. Pat. No. 5,036,057. Recently $GABA_B$-receptor agonists have been shown to inhibit TLOSR which is disclosed in WO 98/11885.

$GABA_B$ Receptor Agonists

GABA (4-aminobutanoic acid) is an endogenous neurotransmitter in the central and peripheral nervous systems. Receptors for GABA have traditionally been divided into $GABA_A$ and $GABA_B$ receptor subtypes. $GABA_B$ receptors belong to the superfamily of G-protein coupled receptors. $GABA_B$ receptor agonists are being described as being of use in the treatment of CNS disorders, such as muscle relaxation in spinal spasticity, cardiovascular disorders, asthma, gut motility disorders such as irritable bowel syndrome (IBS) and as prokinetic and anti-tussive agents. $GABA_B$ receptor agonists have also been disclosed as useful in the treatment of emesis (WO 96/11680) and recently, as mentioned above, in the inhibition of TLOSR (WO 98/11885).

The most studied $GABA_B$ receptor agonist is baclofen (4-amino-3-(chlorophenyl)butanoic acid) disclosed in the Swiss patent. No. CH 449, 046. Baclofen has for several years been used as an antispastic agent. EP 0356128 A2 describes the use of the specific compound (3-aminopropyl)methylphosphinic acid, as a potent $GABA_B$ receptor agonist, in therapy. EP 0181833 A1 discloses substituted 3-aminopropylphosphinic acids which are found to have very high affinities towards $GABA_B$ receptor sites. In analogy to baclofen, the compounds can be used as for instance muscle relaxants. EP 0399949 A1 discloses derivatives of (3-aminopropyl)methylphosphinic acid which are described as potent $GABA_B$ receptor agonists. These compounds are stated to be useful as muscle relaxants. EP 0463969 A1 and FR 2722192 A1 are both applications related to 4-aminobutanoic acid derivatives having different heterocyclic substituents at the 3-carbon of the butyl chain. Structure-activity relationships of several phosphinic acid analogues with respect to their affinities to the $GABA_B$ receptor as well as their muscle relaxant effect are discussed in *J. Med. Chem.* (1995), 38, 3297–3312.

Structure-activity relationships of several phosphinic acid analogues with respect to their affinities to the $GABA_B$ receptor as well as their muscle relaxant effect are discussed in *J. Med. Chem.* (1995), 38, 3297–3312. In addition, some sulphinic acid analogues and their $GABA_B$ receptor activities are disclosed in Bioorg. & Med. Chem. Lett. (1998), 8, 3059–3064.

OUTLINE OF THE INVENTION

The present invention provides novel compounds of the formula I

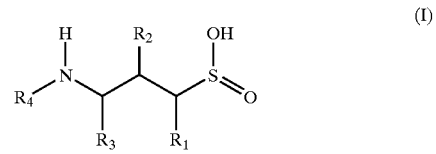

(I)

wherein $R_1$ represents hydrogen, hydroxy, $C_1$–$C_7$ alkyl, $C_1$–$C_7$ alkoxy or halogen;

$R_2$ represents hydrogen, hydroxy, mercapto, halogen, or an oxo group;

$R_3$ represents hydrogen or $C_1$–$C_7$ alkyl (optionally substituted with hydroxy, mercapto, $C_1$–$C_7$ alkoxy, $C_1$–$C_7$ thioalkoxy, aryl or heteroaryl), aryl or heteroaryl;

$R_4$ represents hydrogen, $C_1$–$C_7$ alkyl (optionally substituted with aryl or heteroaryl), aryl or heteroaryl;

and pharmaceutically acceptable salts, solvates and the stereoisomers thereof, with the exceptions of:

(3-aminopropyl)sulphinic acid;

the racemate of (3-amino-1-methylpropyl)sulphinic acid the racemate of (3-amino-3-methylpropyl)sulphinic acid (methyl-3-aminopropyl)sulphinic acid (N-benzyl-3-aminopropyl)sulphinic acid the racemate of (3-amino-2-hydroxypropyl)sulphinic acid (N-(4-chlorophenylmethyl)-3-aminopropyl)sulphinic acid (N-(2-phenylethyl)-3-aminopropyl)sulphinic acid According to one embodiment of the invention the novel compound is selected from the group consisting of (3-amino-2-fluoropropyl)sulphinic acid, (2S)-(3-amino-2-fluoropropyl)sulphinic acid, (2R)-(3-amino-2-fluoropropyl) sulphinic acid, (2S)-(3-amino-2-hydroxypropyl)sulphinic acid, (2R-(3-amino-2-hydroxypropyl)sulphinic acid and (3-amino-2-oxopropyl)sulphinic acid.

Within the scope of the invention, it is to be understood that when $R_2$ is an oxo group the bond between $R_2$ and the carbon is a double bond.

Within the invention $C_1$–$C_7$ alkyl can be straight, branched or cyclic alkyl and is, for example, $C_1$–$C_4$ alkyl, such as methyl, ethyl, n-propyl or n-butyl, also isopropyl, isobutyl, secondary butyl or tertiary butyl, but may also be a $C_5$–$C_7$ alkyl group such as a pentyl, hexyl or heptyl group.

$C_1$–$C_7$ alkoxy is, for example, $C_1$–$C_4$ alkoxy, such as methoxy, ethoxy, n-propoxy or n-butoxy, also isopropoxy, isobutoxy, secondary butoxy or tertiary butoxy, but may also be a $C_5$–$C_7$ alkoxy group, such as a pentoxy, hexoxy or heptoxy group.

$C_1$–$C_7$ thioalkoxy is, for example, $C_1$–$C_4$ thioalkoxy, such as thiomethoxy, thioethoxy, n-thiopropoxy or n-thiobutoxy, also thioisopropoxy, thioisobutoxy, secondary thiobutoxy or tertiary thiobutoxy, but may also be a $C_5$–$C_7$ thioalkoxy group, such as a thiopentoxy, thiohexoxy or thioheptoxy group.

Halogen as used herein is anyone of chlorine, fluorine, bromine or iodine.

The herein used term aryl means aromatic rings with 6–14 carbon atoms including both single rings and polycyclic compounds, such as benzyl or naphtyl, optionally substituted with one or more substituents such as membered rings optionally substituted with one or more substituents such as $C_1$–$C_7$ alkyl, $C_1$–$C_7$ alkoxy, halogen, $C_1$–$C_7$ thioalkoxy, hydroxy, mercapto, carboxylic acid, carboxylic acid ester, carboxylic acid amide or nitrile.

The term heteroaryl as used herein means aromatic rings with 5–14 carbon atoms, including both single rings and polycyclic compounds, in which one or several of the ring atoms is either oxygen, nitrogen or sulphur. The heteroaryl is optionally substituted with one or more substituents such as $C_1$–$C_7$ alkyl, $C_1$–$C_7$ alkoxy, $C_1$–$C_7$ thioalkoxy, halogen, hydroxy, mercapto, carboxylic acid, carboxylic acid ester, carboxylic acid amide or nitrile.

The compounds according to formula I of the invention are of amphoteric nature and may be presented in the form of internal salts. They can also form acid addition salts and salts with bases. Such salts are particularly pharmaceutically acceptable acid addition salts, as well as pharmaceutically acceptable salts formed with bases. Suitable acids for the formation of such salts include, for example, mineral acids such as hydrochloric, hydrobromic, sulfuric, or phosphoric acid or organic acids such as sulfonic acids and carboxylic acids. Salts with bases are, for example, alkali metal salts, e.g. sodium or potassium salts, or alkaline earth metal salts, e.g. calcium or magnesium salts, as well as ammonium salts, such as those with ammonia or organic amines. The salts may be prepared by conventional methods.

When one or more stereocentre is present in the molecule, the compounds according to formula I can be in the form of a stereoisomeric mixture, i.e. a mixture of diastereomers and/or racemates, or in the form of the single stereoisomers, i.e. the single enantiomer and/or diastereomer. The compounds can also be in the form of solvates, e.g. hydrates.

The compounds according to the formula I can be used for the inhibition of TLOSR, and thus for the treatment of gastro-oesophageal reflux disease. The said inhibition of TLOSR also implies that the said compounds of formula I can be used for the treatment of regurgitation in infants. Effective management of regurgitation in infants would be an important way of managing failure to thrive due to excessive loss of ingested nutrient. Furthermore the compounds can be used for the treatment of GORD-related or non-GORD related asthma, belching, coughing, pain, cocaine addiction, hiccups, IBS, dyspepsia, emesis and nociception.

One aspect of the invention is the use of the compounds of formula I

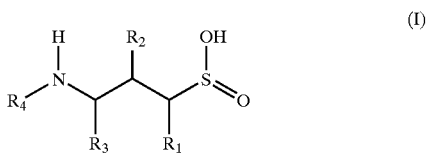

wherein
$R_1$ represents hydrogen, hydroxy, $C_1$–$C_7$ alkyl, $C_1$–$C_7$ alkoxy or halogen;
$R_2$ represents hydrogen, hydroxy, mercapto, halogen, or an oxo group;
$R_3$ represents hydrogen or $C_1$–$C_7$ alkyl (optionally substituted with hydroxy, mercapto, $C_1$–$C_7$ alkoxy, $C_1$–$C_7$ thioalkoxy, aryl or heteroaryl), aryl or heteroaryl;
$R_4$ represents hydrogen, $C_1$–$C_7$ alkyl (optionally substituted with aryl or heteroaryl), aryl or heteroaryl;
and pharmaceutically acceptable salts, solvates and the stereoisomers thereof, in the manufacture of a medicament for the inhibition of TLOSR and thus for the treatment of gastro-oesophageal reflux disease, regurgitation in infants and also for the treatment of GORD-related or non-GORD related asthma, belching, coughing, pain, cocaine addiction, hiccups, IBS, dyspepsia, emesis and nociception.

Another aspect of the invention is a method for the inhibition of TLOSR, for the treatment of gastro-oesophageal reflux disease, regurgitation in infants and also for the treatment of GORD-related or non-GORD related asthma, hyperkinesia, belching, coughing, pain, cocaine addiction, alcohol withdrawal, nicotine dependence, hiccups, IBS, dyspepsia, emesis and nociception, which method comprises treating a subject suffering from said condition with a pharmacuetical preparation comprising a compound of the formula I

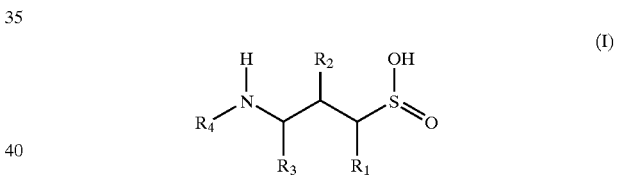

wherein
$R_1$ represents hydrogen, hydroxy, $C_1$–$C_7$ alkyl, $C_1$–$C_7$ alkoxy or halogen;
$R_2$ represents hydrogen, hydroxy, mercapto, halogen, or an oxo group;
$R_3$ represents hydrogen or $C_1$–$C_7$ alkyl (optionally substituted with hydroxy, mercapto, $C_1$–$C_7$ alkoxy, $C_1$–$C_7$ thioalkoxy, aryl or heteroaryl), aryl or heteroaryl;
$R_4$ represents hydrogen, $C_1$–$C_7$ alkyl (optionally substituted with aryl or heteroaryl), aryl or heteroaryl;
and pharmaceutically acceptable salts, solvates and the stereoisomers thereof.

A further aspect is a pharmaceutical preparation comprising the compounds of the invention comprising as active ingredient a therapeutically acceptable amount of a compound according to formula I optionally in association with diluents, excipients or inert carriers.

The wording "TLOSR", transient lower oesophageal sphincter relaxations, is herein defined in accordance with Mittal, R. K, Holloway, R. H., Penagihi, R., Blackshaw, L. A., Dent, J., 1995; *Transient lower esophageal sphincter relaxation. Gastroenterology* 109, pp. 601–610.

The wording "reflux" is herein defined as fluid from the stomach being able to pass into the esophagus, since the mechanical barrier is temporarily lost at such times.

The wording "GORD", gastro-oesophageal reflux disease, is herein defined in accordance with *van Heerwarden, M. A., Smout A. J. P. M., 2000; Diagnosis of reflux disease. Bailliere's Clin. Gastroenterol.* 14, pp. 759–774.

The term "therapy" also includes "prophylaxis" unless there are specific indications to the contrary. The terms "therapeutic" and "therapeutically" should be construed accordingly.

Preparation

The compounds according to formula I of the present invention may be prepared by one of the following methods.

A) A compound of formula II

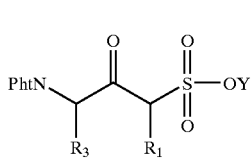

(II)

in which $R_1$ and $R_3$ are as defined above in formula I, Pht is a protecting group such as phtalimido and Y is hydrogen or a protecting group such as $C_1$–$C_7$ alkyl, which compound of formula II may have been synthesized by a condensation reaction according to Scheme 1 employing an appropriate N-protected amino acid ester in which $R_3$ is as defined above, W is a protecting group such as $C_1$–$C_7$ alkyl and Pht is as defined in formula II, and a suitable protected sulphonic acid derivative in which $R_1$ is as defined above in formula I and Y is as defined in formula II, and a base such as lithium diisopropylamide, Scheme 1

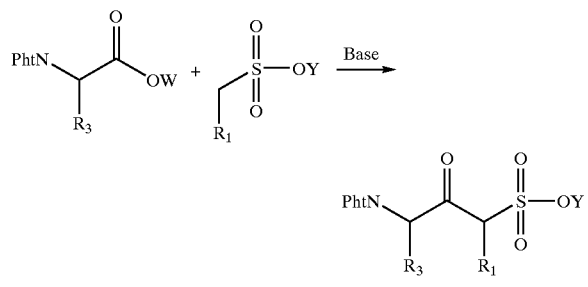

is a) optionally converted by a ketal formation reaction in order to protect the keto group, a hydrolytic reaction followed by a deoxohalogenation reaction in order to obtain a sulphonic acid halide, a hydrazinolysis in order to detach the N-protective group and at the same time obtain a sulphinic acid derivative, optionally an N-alkylation reaction in order to introduce $R_4$ if $R_4$ is desired to be not equal to hydrogen, and thereafter a hydrolytic reaction to obtain a compound of formula III

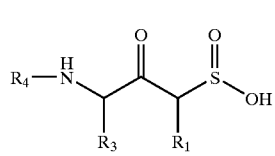

(III)

wherein $R_1$, $R_3$ and $R_4$ are as defined above in formula I, and optionally convert the above resulting compound III into another chemical compound of the formula III and/or separate a resulting mixture of isomers into the individual isomers and/or convert a resulting salt into the free compound of the formula III and/or into another salt and/or convert a resulting free compound of the formula III into a salt to correspond to the above definition, or b) converted by a reductive reaction in order to reduce the keto group, a hydrolytic reaction followed by a deoxohalogenation reaction in order to obtain a sulphonic acid halide, a hydrazinolysis in order to detach the N-protective group and at the same time obtain a sulphinic acid derivative, optionally an N-alkylation reaction in order to introduce $R_4$ if $R_4$ is desired to be not equal to hydrogen, and thereafter a hydrolytic reaction to obtain a compound of formula IV

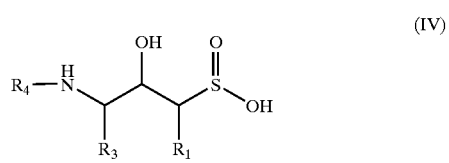

(IV)

wherein $R_1$, $R_3$ and $R_4$ are as defined above in formula I, and optionally convert the above resulting compound IV into another chemical compound of the formula IV and/or separate a resulting mixture of isomers into the individual isomers and/or convert a resulting salt into the free compound of the formula IV and/or into another salt and/or convert a resulting free compound of the formula IV into a salt to correspond to the above definition, or c) converted by a reductive reaction followed by a deoxohalogenation reaction, a hydrolytic reaction followed by a deoxohalogenation reaction in order to obtain a sulphonic acid halide, a hydrazinolysis in order to detach the N-protective group and at the same time obtain a sulphinic acid derivative, optionally an N-alkylation reaction in order to introduce $R_4$ if $R_4$ is desired to be not equal to hydrogen, and thereafter a hydrolytic reaction to obtain a compound of formula V

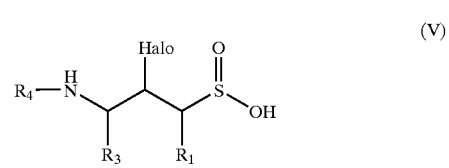

(V)

wherein $R_1$, $R_3$ and $R_4$ are as defined above in formula I and Halo is a halogen atom, and optionally convert the above resulting compound V into another chemical compound of the formula V and/or sepatate a resulting mixture of isomers into the individual isomers and/or convert a resulting salt into the free compound of the formula V and/or into another salt and/or convert a resulting free compound of the formula V into a salt to correspond to the above definition; or B) a compound of formula VI

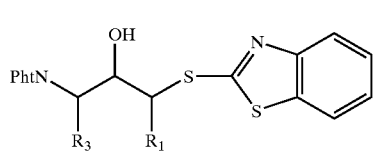

(VI)

in which $R_1$, $R_2$ and $R_3$ are as defined above in formula I, Pht is a protecting group such as phtalimido, which compound of formula VI may have been synthesized by a reaction according to Scheme 2 employing an 2,3-epoxypropyl derivative, such as an appropriate N-protected 2,3-epoxypropylanine derivative, in which $R_1$ and $R_3$ are as defined above in formula I and Pht is as defined above in formula VI, and 2-mercaptobenzothiazole and a base, Scheme 2

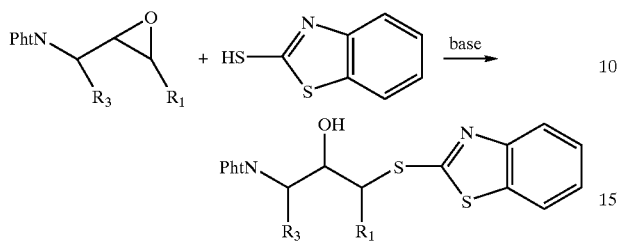

is
a) optionally converted by a hydrazinolysis followed by an acylation reaction if the N-protective group is desired to be changed from a phtalimido group to for instance a t-Boc group, optionally an N-alkylation reaction in order to introduce $R_4$ if $R_4$ is desired to be not equal to hydrogen, an oxidation reaction followed by a reduction reaction in order to obtain a sulphinic acid, and thereafter a hydrolytic reaction to obtain a compound of formula IV

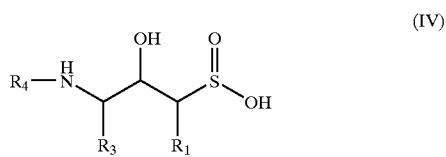

(IV)

wherein $R_1$, $R_3$ and $R_4$ are as defined above in formula I, and optionally convert the above resulting compound IV into another chemical compound of the formula IV and/or sepatate a resulting mixture of isomers into the individual isomers and/or convert a resulting salt into the free compound of the formula IV and/or into another salt and/or convert a resulting free compound of the formula IV into a salt to correspond to the above definition, or b) optionally converted by a hydrazinolysis followed by an acylation reaction if the N-protective group is desired to be changed from phtalimido group to for instance a t-Boc group, optionally an N-alkylation reaction in order to introduce $R_4$ if $R_4$ is desired to be not equal to hydrogen, an oxidation reaction followed by a ketal formation reaction, an oxidation reaction followed by a reduction reaction in order to obtain a sulphinic acid, and thereafter a hydrolytic reaction to obtain a compound of formula VII

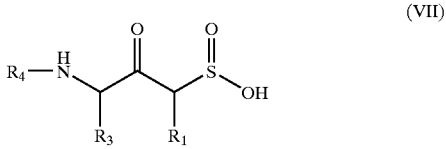

(VII)

wherein $R_1$, $R_3$ and $R_4$ are as defined above in formula I, and optionally convert the above resulting compound VII into another chemical compound of the formula VII and/or sepatate a resulting mixture of isomers into the individual isomers and/or convert a resulting salt into the free compound of the formula VII and/or into another salt and/or convert a resulting free compound of the formula VII into a salt to correspond to the above definition, or c) optionally converted by a hydrazinolysis followed by an acylation reaction if the N-protective group is desired to be changed from phtalimido group to for instance a t-Boc group, optionally an N-alkylation reaction in order to introduce $R_4$ if $R_4$ is desired to be not equal to hydrogen, a deoxohalogenation reaction, an oxidation reaction followed by a reduction reaction in order to obtain a sulphinic acid, and thereafter a hydrolytic reaction to obtain a compound of formula VIII

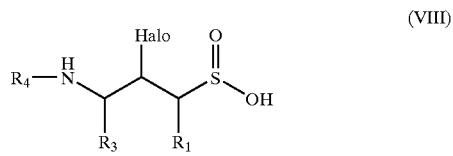

(VIII)

wherein $R_1$, $R_3$ and $R_4$ are as defined above in formula I, and Halo is a halogen atom, and optionally convert the above resulting compound VIII into another chemical compound of the formula VIII and/or sepatate a resulting mixture of isomers into the individual isomers and/or convert a resulting salt into the free compound of the formula VIII and/or into another salt and/or convert a resulting free compound of the formula VIII into a salt to correspond to the above definition; or C) a compound of formula IX

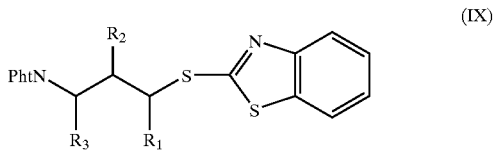

(IX)

in which $R_1$, $R_2$ and $R_3$ are as defined above in formula I, which compound of formula IX may have been synthesized by two subsequently substitution reactions according to Scheme 3 employing a compound in which $R_1$, $R_2$ and $R_3$ are as defined above in formula I, $L_1$ and $L_2$ are leaving groups, and potassium phtalimid followed by 2-mercaptobenzothiazole and a base, Scheme 3

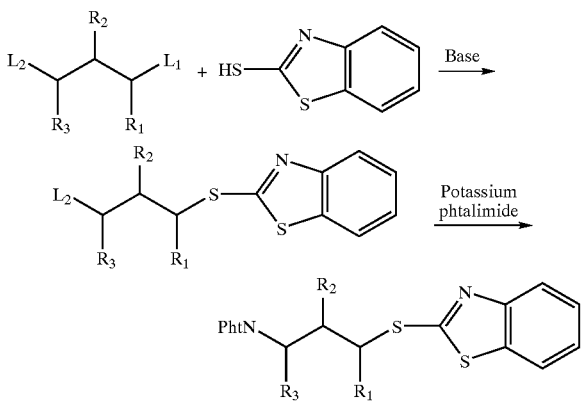

optionally is converted by a hydrazinolysis followed by an acylation reaction if the N-protective group is desired to be changed from phtalimido group to for instance a t-Boc group, optionally an N-alkylation reaction in order to introduce $R_4$ if $R_4$ is desired to be not equal to hydrogen, an oxidation reaction followed by a reduction reaction in order to obtain a sulphinic acid, and thereafter a hydrolytic reaction to obtain a compound of formula I

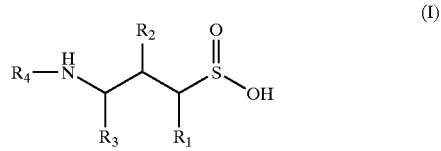

(I)

wherein $R_1$ and $R_4$ are as defined above in formula I, and optionally convert the above resulting compound I into another chemical compound of the formula I and/or separate a resulting mixture of isomers into the individual isomers and/or convert a resulting salt into the free compound of the formula I and/or into another salt and/or convert a resulting free compound of the formula I into a salt to correspond to the above definition.

DETAILED DESCRIPTION OF THE INVENTION

The invention is described more in detail by the following non-limiting examples.

EXAMPLE 1

(2S)-(3-Amino-2-hydroxypropyl)sulphinic acid tert-Butyl (2S)-3-(1,3-benzothiazol-2-ylsulphonyl)-2-hydroxypropylcarbamate (9.30 g, 25.0 mmol) was dissolved in ethanol (100 mL) and then cooled to 0° C. Solid sodium borohydride (1.89 g, 50.0 mmol) was added and the reaction was then warmed to rt and stirred overnight. The reaction was then re-cooled to 0° C. and was quenched by the addition of ethyl acetate/HCl (15 mL) and then allowed to stir for 1.5 h. The solvents were removed under reduced pressure and the residue was purified by ion exchange chromatography (Dowex® 50WX-8-200, H⁺ form). The crude product was suspended in 1:1 methanol/water, loaded onto the resin column and washed with 1:1 methanol/water. The eluent was changed to 1:1 methanol/concentrated ammonium hydroxide to remove the product. Concentration under reduced pressure of the fractions containing product afforded a solid which was triturated with methanol to afford (2S)-(3-amino-2-hydroxypropyl)sulphinic acid (1.51 g, 43%) as a white solid. Data for afford (2S)-(3-amino-2-hydroxypropyl)sulphinic acid: mp=206–208° C.; APCI mass spectrum m/z=140; Optical Rotation $[\alpha]_D^{25}$=+86.94° (c=1.0, Water); $^1$H NMR (300 MHz, $D_2O$) δ 4.14 (m, 1H), 3.11 (dd, J=13 Hz, J=3 Hz, 1H), 2.91 (dd, J=13 Hz, J=9 Hz, 1H), 2.61 dd, J=13 Hz, J=9 Hz, 1H), 2.30 (dd, J=13 Hz, J=4 Hz, 1H).

EXAMPLE 2

(2R)-(3-Amino-2-hydroxypropyl)sulphinic acid tert-Butyl (2R)-3-(1,3-benzothiazol-2-ylsulphonyl)-2-hydroxypropylcarbamate (6.47 g, 17.3 mmol) was dissolved in ethanol (100 mL) and then cooled to 0° C. Solid sodium borohydride (1.70 g, 44.9 mmol) was added and the reaction was then warmed to room temperature and stirred overnight. The reaction was then re-cooled to 0° C. and was quenched by the addition of ethyl acetate/HCl (100 mL) and then allowed to stir for 2 h. The solvents were removed under reduced pressure and the residue was purified by ion exchange chromatography (Dowex® 50WX-8-200, H⁺ form). The crude product was suspended in 1:1 methanol/water, loaded onto the resin column and washed with 1:1 methanol/water. The eluent was changed to 1:1 methanol/concentrated ammonium hydroxide to remove the product. Concentration under reduced pressure of the fractions containing product afforded a solid which was triturated with methanol to afford (2R)-(3-amino-2-hydroxypropyl)sulphinic acid (1.03 g, 43%) as a white solid. Data for (2R)-(3-amino-2-hydroxypropyl)sulphinic acid: mp=210° C.; APCI mass spectrum m/z=140; Optical Rotation $[\alpha]_D^{25°}$ c.=−88.60 (c=1.00, Water); $^1$H NMR (300 MHz, $D_2O$) δ 4.17 (m, 1H), 3.14 (m, 1H), 2.95 (dd, J=13 Hz, J=9 Hz, 1H), 2.63 (dd, J=13 Hz, J=9 Hz, 1H), 2.33 (dd, J=13 Hz, J=4 Hz, 1H).

The following intermediates were used in the preparation of compounds of the invention.

EXAMPLE 3

3-Amino-(2R)-2-fluoro-1-propanesulfinic acid

Carbamic acid, [(2R)-3-[(1,1-dimethylethyl)sulfonyl]-2-fluoropropyl]-, 1,1-dimethylethyl ester (5 g, 16.8 mmol) was dissolved in methylene chloride (60 mL) and cooled to 0° C. Neat trifluoromethanesulfonic acid (12.5 mL, 141 mmol) was added dropwise over 3 minutes to the rapidly stirred solution. After 2 h the methylene chloride is removed on a rotary evaporator, the residue is cooled to 0° C. and then water (30 mL) is added. Any precipitate formed is removed by filtration and then the solution is loaded onto a Dowex 50WX8-200 column which has been pre-washed with 1:1 methanol/water and then with just water. The column is eluted with water until all of the triflic acid is off and then the product is removed with 3:1 methanol/concentrated ammonium hydroxide. Concentration of the appropriate fractions provides crude 3-Amino-2-fluoro-(2R)-1-propanesulfinic acid. Purification by silica gel column chromatography eluting with (6:3:1 methylene chloride/methanol/concentrated ammonium hydroxide provided pure title compound (782 mg, 33%) as a white solid.

Data: mp 136–138° C., $R_f$=0.35 (methylene chloride, methanol, concentrated ammonium hydroxide (6:3:1), ninhydrin development), m/z=140 (M−H), $^1$H NMR (300 MHz, $D_2O$), δ 5.22 (m, 0.5H), 5.06 (m, 0.5H), 3.32 (m, 2H), 2.88 (m, 1H), 2.48 (m, 1H).

Intermediates

EXAMPLE I1 tert-Butyl (2S)-3-(1,3-benzothiazol-2-ylsulphonyl)-2-hydroxypropylcarbamate tert-Butyl (2S)-3-(0,1,3-benzothiazol-2-ylthio)-2-hydroxypropylcarbamate (33.5 g, 68.8 mmol, i.e. maximum theoretical amount) was dissolved in methylene chloride (750 mL) and then treated with 3-chloroperoxybenzoic acid (29.7 g, 172 mmol) in small portions. After the reaction was stirred for 3 days, the mixture was washed sequentially with a solution of sodium bicarbonate followed by a solution of saturated sodium chloride. The organic layer was dried with magnesium sulfate, filtered and concentrated under reduced pressure to afford crude tert-butyl (2S)-3-(1,3-benzothiazol-2-ylsulphonyl)-2-hydroxypropylcarbamate. Purification on silica gel eluting with 4:1 methylene chloride/ethyl acetate gave tert-butyl (2S)-3-(1,3-benzothiazol-2-ylsulphonyl)-2-hydroxypropylcarbamate (9.30 g, 36% from tert-butyl (2S)-3-(1,3-benzothiazol-2-ylthio)-2-hydroxypropylcarbamate) as a white solid. Data for tert-butyl (2S)-3-(1,3-benzothiazol-2-ylsulphonyl)-2-hydroxypropylcarbamate:

¹H NMR (300 MHz, CDCl₃) δ 8.22 (d, 1H), 8.04 (d, 1H), 7.70–7.60 (m, 2H), 5.03 (m, 1H), 4.48 (m, 1H), 4.19 (m, 1H), 3.72 (m, 2H), 3.50–3.30 (m, 2H), 1.43 (s, 9H).

EXAMPLE I2 tert-Butyl (2S)-3-(13-benzothiazol-2-ylthio)-2-hydroxypropylcarbamate

A suspension of N-[(2S)-3-(1,3-benzothiazol-2-ylthio)-2-hydroxypropyl]-phthalimide (25.5 g, 68.8 mmol) in EtOH (550 mL) was treated with hydrazine hydrate (5.3 mL, 109 mmol) and heated to 50° C. for 3 h. The reaction was cooled, filtered and the solvents were removed under reduced pressure. The crude residue was taken up in methylene chloride (250 mL) and treated with di-tert-butyl dicarbonate (22.5 g, 103 mmol) then allowed to stir overnight. The solvents were then removed under reduced pressure to give crude tert-butyl (2S)-3-(1,3-benzothiazol-2-ylthio)-2-hydroxypropylcarbamate. Purification on silica gel eluting with methylene chloride to start and then switching to ethyl acetate provided tert-butyl (2S)-3-(1,3-benzothiazol-2-ylthio)-2-hydroxypropylcarbamate (33.5 g) as an oil which was contaminated with di-tert-butyl dicarbonate residues. This compound was used directly in the next step. Data for tert-butyl (2S)-3-(1,3-benzothiazol-2-ylthio)-2-hydroxypropylcarbamate: ¹H NMR (300 MHz, CDCl₃) δ 7.85 (d, 1H), 7.76 (d, 1H), 7.45 (dd, 1H), 7.35 (dd, 1H), 5.35 (m, 1H), 5.05 (m, 1H), 4.15 (m, 1H), 3.57–3.40 (m, 3H), 3.35–3.25 (m, 1H), 1.48 (s, 9H).

EXAMPLE I3

N-[(2S)-3-(1.3-Benzothiazol-2-ylthio)-2-hydroxypropyl]-phthalimide

A suspension of N-[(2S)-oxiran-2-ylmethyl]-phthalimide (18.4 g, 90.6 mmol) and 2-mercaptobenzothiazole (15.8 g, 94.5 mmol) in EtOH (530 mL) was heated to reflux for 14.5 h. The reaction was then cooled and concentrated under reduced pressure. The crude mixture was crystallized from ethanol and filtered to provide N-[(2S)-3-(1,3-benzothiazol-2-ylthio)-2-hydroxypropyl]-phthalimide (25.5 g, 76%) as a solid. Data for N-[(2S)-3-(1,3-benzothiazol-2-ylthio)-2-hydroxypropyl]-phthalimide: ¹H NMR (300 MHz, CDCl₃) δ 7.88 (m, 2H), 7.75 (m, 4H), 7.45–7.26 (m, 2H), 5.15 (m, 1H), 4.42 (m, 1H), 4.08–3.88 (m,2H), 3.61 (m, 1H), 3.42 (m, 1H).

EXAMPLE I4

N-[(2S)-Oxiran-2-ylmethyl]-phthalimide

Triphenylphosphine (77.0 g, 294 mmol) and phthalimide (44.2 g, 300 mmol) were combined in THF (330 mL) and cooled to 0° C. A solution of diethyl azodicarboxylate (52.2 g, 300 mmol) and (S)-(−)-glycidol (24.3 g, 328 mmol) in THF (110 mL) was added dropwise to the reaction flask. Once the addition was complete, the reaction was allowed to warm to rt while stirring overnight. The solvents were removed under reduced pressure and the residue was stirred in diethyl ether (1 L) for 1 h. The solids were removed by filtration and the filtrate was concentrated under reduced pressure to give crude N-[(2S)-oxiran-2-ylmethyl]-phthalimide. The crude product was purified by crystallization from ethanol to provide N-[(2S)-oxiran-2-ylmethyl]-phthalimide (18.4 g, 30%) as a white solid. Data for N-[(2S)-oxiran-2-ylmethyl]-phthalimide: Chiral HPLC: 97% ee (Daicel ChiralPak AD column); ¹H NMR (300 MHz, CDCl₃) δ 7.88 (m, 2H), 7.76 (m, 2H), 3.97 (dd, 1H), 3.83 (dd, 1H), 3.27 (m, 1H), 2.82 (m, 1H), 2.71 (m, 1H).

EXAMPLE I5 tert-Butyl (2R)-3-(1.3-benzothiazol-2-ylsulphonyl)-2-hydroxypropylcarbamate tert-Butyl (2R)-3-(1,3-benzothiazol-2-ylthio)-2-hydroxypropylcarbamate (18.0 g, 52.8 mmol) was dissolved in methylene chloride (700 mL) and then treated with 3-chloroperoxybenzoic acid (22.8 g, 132 mmol) in small portions. After the reaction was stirred for 3 days, the mixture was washed sequentially with a solution of sodium bicarbonate followed by a solution of saturated sodium chloride. The organic layer was dried with magnesium sulphate, filtered and concentrated under reduced pressure to afford crude tert-butyl (2R)-3-(1,3-benzothiazol-2-ylsulphonyl)-2-hydroxypropylcarbamate. Purification on silica gel eluting with 4:1 methylene chloride/ethyl acetate gave tert-butyl (2R)-3-(1,3-benzothiazol-2-ylsulphonyl)-2-hydroxypropylcarbamate (6.47 g, 33%) as a white solid. Data for tert-butyl (2R)-3-(1,3-benzothiazol-2-ylsulphonyl)-2-hydroxypropylcarbamate: ¹H NMR (300 MHz, CDCl₃) δ 8.22 (d, 1H), 8.04(d, 1H), 7.70–7.60 (m, 2H), 5.03 (m, 1H), 4.48 (m, 1H), 4.19 (m, 1H), 3.72 (m, 2H), 3.51–3.30 (m,2H), 1.43 (s, 9H).

EXAMPLE I6 tert-Butyl (2R)-3-(1,3-benzothiazol-2-ylthio)-2-hydroxypropylcarbamate

A suspension of N-[(2R)-3-(1,3-benzothiazol-2-ylthio)-2-hydroxypropyl]-phthalimide (22.5 g, 60.7 mmol) in EtOH (500 mL) was treated with hydrazine hydrate (4.0 mL, 82.4 mmol) and heated to 50° C. for 4 h. The reaction was cooled, filtered and the solvents were removed under reduced pressure. The crude residue was taken up in methylene chloride (500 mL) and treated with di-tert-butyl dicarbonate (19.9 g, 91.1 mmol) then allowed to stir overnight. The solvents were then removed under reduced pressure to give crude compound 2. Purification on silica gel eluting with methylene chloride to start and then switching to ethyl acetate provided tert-butyl (2R)-3-(1,3-benzothiazol-2-ylthio)-2-hydroxypropylcarbamate (18.0 g, 87%) as an oil. Data for tert-butyl (2R)-3-(1,3-benzothiazol-2-ylthio)-2-hydroxypropylcarbamate: ¹H NMR (300 MHz, CDCl₃) δ 7.80 (d, 1H), 7.71 (d, 1H), 7.40 (dd, 1H), 7.30 (dd, 1H), 5.35 (m, 1H), 5.00 (m, 1H), 4.10 (m,1H), 3.52–3.35 (m, 3H), 3.30–3.20 (m, 1H), 1.45 (s, 9H).

EXAMPLE I7

N-[(2R)-3-(1,3-Benzothiazol-2-ylthio)-2-hydroxypropyl]-phthalimide

A suspension of compound N-[(2R)-oxiran-2-ylmethyl]-phthalimide (21.1 g, 104 mmol) and 2-mercaptobenzothiazole (17.4 g, 104 mmol) in EtOH (600 mL) was heated to reflux for 16.5 h. The reaction was then cooled and concentrated under reduced pressure. The crude mixture was crystallized from ethanol and filtered to provide N-[(2R)-3-(1,3-benzothiazol-2-ylthio)-2-hydroxypropyl]-phthalimide (22.5 g, 59%) as a yellow solid. Data for N-[(2R)-3-(1,3-benzothiazol-2-ylthio)-2-hydroxypropyl]-phthalimide: ¹H NMR (300 MHz, CDCl₃) δ 7.88 (m, 2H), 7.75 (m, 4H), 7.45–7.26 (m, 2H), 5.18 (m, 1H), 4.42 (m, 1H), 4.08–3.88 (m, 2H), 3.61 (m, 1H), 3.42 (m, 1H).

EXAMPLE I8

N-[(2R)-Oxiran-2-ylmethyl]-phthalimide

Triphenylphosphine (49.5 g, 189 mmol) and phthalimide (28.4 g, 193 mmol) were combined in THF (220 mL) and cooled to 0° C. A solution of diethyl azodicarboxylate (33.6 g, 193 mmol) and (R)-(+)-glycidol (16.4 g, 222 mmol) in THF (75 mL) was added dropwise to the reaction flask. Once the addition was complete, the reaction was allowed to warm to rt while stirring overnight. The solvents were removed under reduced pressure and the residue was stirred in diethyl ether (750 mL) for 1 h. The solids were removed by filtration and the filtrate was concentrated under reduced pressure to give crude N-[(2R)-oxiran-2-ylmethyl]-phthalimide. The crude product was purified by silica gel chromatography using 1:1 heptane/ethyl acetate to provide compound N-[(2R)-oxiran-2-ylmethyl]-phthalimide (19.1 g, 50%) as a white solid. Data for N-[(2R)-oxiran-2-ylmethyl]-phthalimide: $^1$H NMR (300 MHz, CDCl$_3$) δ 7.88 (m, 2H), 7.76 (m, 2H), 3.97 (dd, 1H), 3.83 (dd, 1H), 3.27 (m, 1H), 2.82 (m, 1H), 2.71 (m, 1H).

EXAMPLE I9

Carbamic acid, [(2R)-2-fluoro-3-[(methylsulfonyl)oxy]propyl]-, 1,1-dimethylethyl-ester (intermediate 1 to the compound according to Example 4)

Carbamic acid, [(2R)-2-fluoro-3-hydroxypropyl])-, 1,1-dimethylethyl ester 1627 g (8.43 mol) was dissolved in THF (7100 mL) and treated with triethylamine (1117 g, 11 mol) and the resulting mixture was cooled to 0–5° C. Methanesulfonylchloride (940 g, 8.21 mol) was introduced dropwise at such a rate that the temperature was maintained at 0–5° C. After 30 minutes additional triethylamine (225 g, 2.22 mol) and methanesulfonyl chloride (185 g, 1.62 mol) were added. After 2 hours the mixture was quenched by the addition of water (8000 mL) while keeping the temperature below 10° C., extracted with tert-butyl methyl ether (8000 mL) and the organic phase was separated. The solution was washed with water (5000 mL), dried over anhydrous magnesium sulfate, filtered and concentrated to a residue that became a slurry as the concentration neared completion. The slurry was then treated with hexane (3000 mL), cooled to 0–5° C., filtered and the solids were washed with hexane (1000 mL). The filtrate was concentrated to a residue and a second crop of product was isolated by crystallization from the hexane solutions. The two crops were analyzed to show that they were pure product samples and thus were combined and dried in a vacuum oven at 40–50° C. to provide a white crystalline solid (1240 g, 53%).

Data: $^1$H NMR (300 MHz, CDCl$_3$) δ4.89 (m, 1.5H), 4.74 (m, 0.5H), 4.43 (m, 1H), 4.36 (m, 1H), 3.50 (m, 1H), 3.43 (m, 1H), 3.08 (s, 3H), 1.45 (s, 9H).

EXAMPLE I10

Carbamic acid, [(2R)-3-[(1,1-dimethylethyl)thio]-2-fluoropropyl]-, 1,1-dimethylethyl ester (intermediate 2 to the compound according to Example 4)

Carbamic acid, [(2R)-2-fluoro-3-[(methylsulfonyl)oxy]propyl]-, 1,1-dimethylethyl ester (13.0 g, 47.9 mmol), 2-methyl-2-propanethiol (5.39 mL, 47.8 mmol) and cesium carbonate (23.4 g, 71.8 mmol) were combined in acetonitrile (300 mL) and heated to reflux for 3.5 h. The crude reaction mixture was filtered to remove solids and the filtrate was concentrated under reduced pressure. Purification by silica gel column chromatography eluting with 90:10 methylene chloride/ethyl acetate afforded carbamic acid, [(2R)-3-[(1,1-dimethylethyl)thio]-2-fluoropropyl]-, 1,1-dimethylethyl ester as an oil (11.1 g, 87%).

Data: $^1$H NMR (300 MHz, CDCl$_3$) δ 4.87 (br s, 1H), 4.72 (m, 0.5H), 4.58 (m, 0.5H), 3.59 (m, 1H), 3.30 (m, 1H), 2.78 (m, 2H), 1.32 (s, 9H), 1.45 (s, 9H).

EXAMPLE I11

Carbamic acid, [(2R)-3-[(11-dimethylethyl)sulfonyl]-2-fluoropropyl]-1,1-dimethylethyl ester (intermediate 3 to the compound according to Example 4)

Carbamic acid, [(2R)-3-[(1,1-dimethylethyl)thio]-2-fluoropropyl]-, 1,1-dimethylethyl ester (11.1 g, 41.9 mmol) was dissolved in methylene chloride (300 mL) and cooled in an ice water bath. 3-Chloroperoxybenzoic acid (23.3 g, 77%, 0.10 mol) was added portionwise then the mixture was allowed to warm to room temperature. After 2 hours dilute potassium carbonate solution was added and the reaction mixture was extracted with methylene chloride, dried over sodium sulfate, filtered and concentrated under reduced pressure to afford crude carbamic acid, [(2R)-3-[(1,1-dimethylethyl)sulfonyl]-2-fluoropropyl]-, 1,1-dimethylethyl ester. Purification by silica gel column chromatography eluting with 90:10 methylene chloride/ethyl acetate afforded compound the title compound as a white solid (8.12 g, 65%).

Data: $^1$H NMR (300 MHz, CDCl$_3$) δ 5.28 (m, 0.5H), 5.12 (m, 0.5H), 4.98 (br s, 1 H), 3.65–3.27 (m, 4H), 1.48 (s, 9H), 1.46 (s, 9H).

Pharmaceutical Preparations

The compound according to formula I of the present invention can be used as an active ingredient in a pharmaceutical preparation for oral, rectal, epidural, intravenous, intramuscular, subcutanous, nasal administration and administration by infusion or for any other suitable route of administration. Preferably the way of administration is oral or by injection/infusion;

The pharmaceutical preparations contain a compound of the present invention in combination with one or more pharmaceutically acceptable ingredients. The finished dosage forms are manufactured by known pharmaceutical processes. Usually the amount of active compounds is between 0.1–95% by weight of the preparation, preferably between 0.2–20% by weight in preparations for parenteral use and preferably between 1–50% by weight in preparations for oral administration.

In the preparation of pharmaceutical preparations containing a compound of the present invention in the form of solid dosage units for oral administration, the compound selected may be mixed with solid pharmaceutically acceptable ingredients (among these for instance disintegrating agents and lubricating agents). The mixture is then processed into granules, tablets, capsules or sachets.

Dosage units for rectal administration may be prepared in the form of suppositories; in the form of a gelatine rectal capsule; in the form of a ready-made micro enema; or in the form of a dry micro enema formulation to be reconstituted in a suitable solvent just prior to administration.

Liquid preparations for oral administration may be prepared in the form of syrups or suspensions, or in the form of a dry mixture to be reconstituted with a suitable solvent prior to use.

Solutions for parenteral administration may be prepared as a solution of a compound of the invention in a pharmaceutically acceptable solvent and are dispensed into ampoules or vials. They may also be prepared as a dry preparation to by reconstituted with a suitable solvent extemporaneously before use.

The typical daily dose of the active compound will depend on various factors such as for example the individual requirement of each patient, the route of administration and the disease. In general, dosages will be in the range of from 1 µg to 100 mg per day and kg body weight. A further aspect of the invention is to administer the active compound in a dose of from 10 µg to 20 mg per day and kg body weight. The active ingredient may in one embodiment be administered once daily. In another embodiment it may administered several times daily. In yet another embodiment it may administered less often than once daily.

Biological Studies
[³H]GABA Radioligand Binding Assay

Rat synaptic membranes were prepared from the whole brain of Sprague Dawley male rats essentially as described previously (Zukin, et al. (1974) Proc. Natl. Acad. USA 71, 4802–4807). The [³H]GABA competition assay, modified from Olpe et al ((1990) Eur. J. Pharmacol. 187, 27–38), was performed in 200 µl TCI (Tris Calcium Isoguvacine) buffer (50 mM Tris (tri(hydroxymethyl)aminomethane), pH 7.4, 2.5 mM CaCl₂ and 40 µm isoguvacine) containing 20 nM [³H]GABA (specific activity: 3 Tera Becquerel (TBq)/mmol), test compound or solvent and 80 µg synaptic membrane protein using 96-well plates. After incubation for 12–20 min at room temperature, incubations were terminated by rapid filtration through a glass fiber filter (Printed filtermat B filters, Wallac), which had been pretreated with 0.3% polyethyleneimine, using a 96-well plate cell harvester (Skatron or Tomtec). The filters were washed with buffer containing 50 mM Tris (tris(hydroxymethyl)aminomethane) and 2.5 mM CaCl₂, pH 7.4, at 4° C. and then dried at 55° C. MeltiLex B/HS scintillator sheet (Wallac) was melted onto the filter, and radioactivity was determined in a Microbeta scintillation counter (Wallac).

Results and Discussion

The compounds of the present invention were found to have high affinities and potencies for the GABA$_B$ receptor as revealed by low IC$_{50}$ and EC$_{50}$ in the binding and ileum assays, respectively. The compounds have also been found to reduce TLOSR when administered i.v. as well as p.o. in animal models. Moreover, CNS side-effects (as measured by reduction in body temperature in the mouse) were not observable or only seen at high doses. Therefore, the difference between therapeutic dose (inhibition of TLOSR in the dog model) and dose causing side-effects (in the mouse model) was unexpectedly high.

What is claimed is:

1. A compound according to formula I

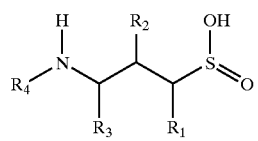

(I)

or a racemate, stereoisomer or a mixture thereof,
wherein:
R$_1$ represents hydrogen;
R$_2$ represents hydroxy, fluoro or an oxo group;
R$_3$ represents hydrogen; and
R$_4$ represents hydrogen;
with the exception of the racemate of (3-amino-2-hydroxypropyl)sulphinic acid, wherein the compound, racemate or a stereoisomer thereof may exist in the form of a pharmaceutically acceptable salt and/or solvate thereof.

2. The compound according to claim 1 which is (3-amino-2-fluoropropyl)sulphinic acid.

3. The compound according to claim 2 which is (2S)-(3-amino-2-fluoropropyl)sulphinic acid.

4. The compound according to claim 2 which is (2R)-(3-amino-2-fluoropropyl)sulphinic acid.

5. The compound according to claim 1 which is (2S)-(3-amino-2-hydroxypropyl)sulphinic acid.

6. The compound according to claim 1 which is (2R)-(3-amino-2-hydroxypropyl)sulphinic acid.

7. The compound according to claim 1 which is (3-amino-2-oxopropyl)sulphinic acid.

8. A method for the inhibition of transient lower oesophageal sphincter relaxations, the method comprising administering to a patient in need of such inhibition a therapeutically effective amount of a compound according to formula I

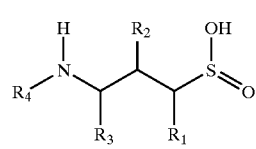

(I)

or a racemate, stereoisomer or a mixture thereof,
wherein:
R$_1$ represents hydrogen;
R$_2$ represents hydroxy, fluoro or an oxo group;
R$_3$ represents hydrogen; and
R$_4$ represents hydrogen;
optionally together with a pharmaceutically acceptable carrier,
wherein the compound, racemate or a stereoisomer thereof may exist in the form of a pharmaceutically acceptable salt and/or solvate thereof.

9. A method for the treatment of gastro-oesophaegeal reflux disease, comprising administering to a patient in need of such treatment a therapeutically effective amount of a compound according to formula I

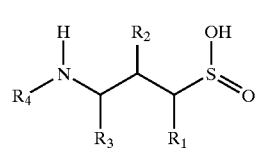

(I)

or a racemate, stereoisomer or a mixture thereof,
wherein:
R$_1$ represents hydrogen;
R$_2$ represents hydroxy, fluoro or an oxo group;
R$_3$ represents hydrogen; and
R$_4$ represents hydrogen;
optionally together with a pharmaceutically acceptable carrier,
wherein the compound, racemate or a stereoisomer thereof may exist in the form of a pharmaceutically acceptable salt and/or solvate thereof.

10. A method for the treatment of regurgitation in infants, comprising administering to a patient in need of such treatment a therapeutically effective amount of a compound according to formula I

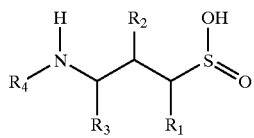

(I)

or a racemate, stereoisomer or a mixture thereof,
wherein:
$R_1$ represents hydrogen;
$R_2$ represents hydroxy, fluoro or an oxo group;
$R_3$ represents hydrogen; and
$R_4$ represents hydrogen;
optionally together with a pharmaceutically acceptable carrier,
wherein the compound, racemate or a stereoisomer thereof may exist in the form of a pharmaceutically acceptable salt and/or solvate thereof.

11. A method for the treatment of GORD-related or non-GORD related asthma, hyperkinesia, belching, coughing, pain, cocaine addiction, alcohol withdrawal, nicotine dependence, hiccups, IBS, dyspepsia, emesis, or nociception, the method comprising administering to a patient in need of such treatment a therapeutically effective amount of a compound according to formula I

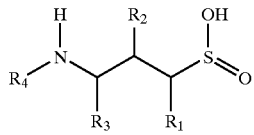

(I)

or a racemate, stereoisomer or a mixture thereof, wherein
$R_1$ represents hydrogen;
$R_2$ represents hydroxy, fluoro or an oxo group;
$R_3$ represents hydrogen;
$R_4$ represents hydrogen;
optionally together with a pharmaceutically acceptable carrier,
wherein the compound, racemate or a stereoisomer thereof may exist in the form of a pharmaceutically acceptable salt and/or solvate thereof.

12. A pharmaceutical formulation comprising as active ingredient a therapeutically acceptable amount of a compound according to formula I of claim 1, together with at least one pharmacologically and pharmaceutically acceptable carrier.

13. A compound selected from the group consisting of
tert-Butyl (2S)-3-(1,3-benzothiazol-2-ylsulphonyl)-2-hydroxypropylcarbamate;
tert-Butyl (2S)-3-(1,3-benzothiazol-2-ylthio)-2-hydroxypropylcarbamate;
N-[(2S)-3-(1,3-Benzothiazol-2-ylthio)-2-hydroxypropyl]-phthalimide;
N-[(2S)-Oxiran-2-ylmethyl]-phthalimide in the form of a single enantiomer;
tert-Butyl (2R)-3-(1,3-benzothiazol-2-ylsulphonyl)-2-hydroxypropylcarbamate;
tert-Butyl (2R)-3-(1,3-benzothiazol-2-ylthio)-2-hydroxypropylcarbamate;
N-[(2R)-3-(1,3-Benzothiazol-2-ylthio)-2-hydroxypropyl]-phthalimide; and
N-[(2R)-Oxiran-2-ylmethyl]-phthalimide in the form of a single enantiomer.

* * * * *